United States Patent [19]

Reedy

[11] 4,158,772

[45] Jun. 19, 1979

[54] DEVICE FOR COLLECTING AND ANALYZING MATRIX-ISOLATED SAMPLES

[75] Inventor: Gerald T. Reedy, Lemont, Ill.

[73] Assignee: The United States of America as represented by the United States Department of Energy, Washington, D.C.

[21] Appl. No.: 902,185

[22] Filed: May 2, 1978

[51] Int. Cl.² ............................................... G01T 1/00
[52] U.S. Cl. .................................. 250/338; 250/304; 250/341; 250/343; 250/352; 250/373; 356/244
[58] Field of Search ............... 250/343, 344, 345, 338, 250/340, 341, 352, 304, 372, 373, 439, 455; 356/38, 51, 244, 246; 23/232 C, 254 R; 73/23.1

[56] References Cited

U.S. PATENT DOCUMENTS 3,287,557  11/1966  Bartz ................................ 250/343 X
3,508,836   4/1970  Polchlopek et al. ............ 356/246 X

OTHER PUBLICATIONS

Rochkind, "Infrared Analysis of Multicomponent Gas Mixtures", Analytical Chemistry, vol. 39, No. 6, May 1967, pp. 567-574.
Hallam, Vibrational Spectroscopy of Trapped Species, pp. 31-34, John Wiley & Son, 1973.

Primary Examiner—Davis L. Willis
Attorney, Agent, or Firm—Dean E. Carlson; Frank H. Jackson; Hugh W. Glenn

[57] ABSTRACT

A gas-sample collection device is disclosed for matrix isolation of individual gas bands from a gas chromatographic separation and for presenting these distinct samples for spectrometric examination. The device includes a vacuum chamber containing a rotatably supported, specular carrousel having a number of external, reflecting surfaces around its axis of rotation for holding samples. A gas inlet is provided for depositing sample and matrix material on the individual reflecting surfaces maintained at a sufficiently low temperature to cause solidification. Two optical windows or lenses are installed in the vacuum chamber walls for transmitting a beam of electromagnetic radiation, for instance infrared light, through a selected sample. Positioned within the chamber are two concave mirrors, the first aligned to receive the light beam from one of the lenses and focus it to the sample on one of the reflecting surfaces of the carrousel. The second mirror is aligned to receive reflected light from that carrousel surface and to focus it outwardly through the second lens. The light beam transmitted from the sample is received by a spectrometer for determining absorption spectra.

10 Claims, 4 Drawing Figures

DEVICE FOR COLLECTING AND ANALYZING MATRIX-ISOLATED SAMPLES

CONTRACTUAL ORIGIN OF THE INVENTION

The invention described herein was made in the course of, or under, a contract with the United States Department of Energy.

BACKGROUND OF THE INVENTION

The present invention relates to a cryostatic collection device capable of collecting and storing a plurality of samples isolated in a matrix for presentation to a beam of light or other electromagnetic radiation for absorption spectroscopy. It is particularly applicable as an interfacial component within a system incorporating gas chromatography and infrared spectroscopy for the analysis of gas samples including a number of components.

The device may also have application in systems employing other characterizing electromagnetic radiation including not only infrared light but visible light and ultraviolet light. This present device may also be useful in analytical systems that rely on luminescence, phosphorescence, fluorescence or on laser interrogation, e.g. the laser raman matrix-isolation spectroscopy. For purposes of this application the term "light", unless otherwise specified, is intended to contemplate this broader scope of applications.

Gas chromatographic separations have been useful fundamental tools of chemical research and analysis for some time. Their usefulness is greatly enhanced when the separated components can be conveniently and promptly analyzed. The matrix-isolation technique for presenting samples for spectroscopic examination is also of considerable value in obtaining precise analysis of samples including specific structural information about molecular construction through high-resolution infrared analyses. Previously no satisfactory system has combined these two highly useful techniques.

In matrix-isolation spectroscopy, a particular and distinct sample material is entrapped within a frozen matrix of an inert substance such as argon or krypton gas. This technique permits the retention of the sample in a neutral and noncontaminating matrix material over an extended period of time. Consequently extremely high resolution can be obtained in spectroscopic and other optical types of analyses.

Gas chromatographic systems are employed to separate collected samples into particular components or bands to permit their identification. These type separations are based on the retention of individual gas components on an absorptive surface. In some of the previous systems, components have been collected manually in liquid and gas microcells at ambient or elevated temperature for subsequent analyses. In other systems, a stop-flow mode of operation is incorporated into the chromatographic unit such that gas flow is retarded while infrared spectra of components are taken. In this type system, only a short time is available for analysis and none of the components are retained for duplication of test results. In another commercially available system, gas chromatogram discharge passes through a light pipe for "on the fly" infrared spectroscopy with such as a fourier-transform mode of operation. These existing systems for gas analyses exhibit limited observation time and consequently suffer in both precision and resolution.

PRIOR ART STATEMENT

The following publications describe gas analyses systems in the same general field as the present development, but do not disclose or suggest this invention.

Rochkind, "Infrared Analysis of Multicomponent Gas Mixtures", Analytical Chemistry, Vol. 39, No. 6, May 1967, pages 567–574. This publication describes a matrix-isolation technique in which gas mixtures containing multiple components within matrix material are subjected to infrared analysis. The system does not show separation, capture and storage of the individual components in matrix isolation within a consolidated apparatus for individual spectroscopic examination of the distinct components.

Hallam, Vibrational Spectroscopy of Trapped Species, pages 31–34, John Wiley and Son, 1973. This treatise describes a rotating collection surface on which overlying layers of samples can be collected. It does not present a device for collecting individual samples such as those separated in a gas chromatograph for storage and subsequent spectrometric analysis of individual components within distinct matrices.

SUMMARY OF THE INVENTION

In view of the disadvantages discussed above, it is an object of the present invention to provide a sample collection device for isolating a plurality of distinct samples, each in a separate matrix, for spectroscopic examination.

It is a further object of the invention to provide a device for capturing and storing individual components from a gas chromatographic separation within a neutral matrix material for subsequent infrared spectroscopic examination.

It is a further object to provide a sample collection device for spectroscopic examination in which samples can be held for an extended period of time within matrix material for obtaining high signal-to-noise absorption spectra for enhanced analytical precision.

In accordance with the present invention, a sample collection device is presented in which a specular sample block is rotatably supported on a stationary shaft within a vacuum chamber. The block includes a plurality of cold, reflecting surfaces each for receiving and solidifying a separate deposit of sample within matrix material. Two optical windows are provided in the vacuum chamber walls for receiving and transmitting a beam of electromagnetic radiation through the sample for spectroscopic analysis within a suitable spectrometer. A rotational drive engages the sample block to rotate it on the stationary shaft and present reflecting surfaces for sample deposition and analysis.

In more specific aspects of the invention, a gas chromatography unit is provided for initial separation of the sample gas into its various bands or components. The sample block threadedly engages a stationary spiral-screw shaft to give both rotational and translational motion as the block is rotated. This screw-like motion provides additional tiers in a helical progression for deposition of samples. In other aspects, two concave mirrors are positioned within the vacuum chamber to focus light radiation from the entrance lens onto the sample surface which is then focused by the second mirror onto the center of the second lens for transmission to the spectrometer.

DETAILED DESCRIPTION OF THE DRAWINGS

The present invention is illustrated in the accompanying drawings wherein.

DETAILED DESCRIPTION OF THE PREFERRED EMBODIMENT

Figure 1:
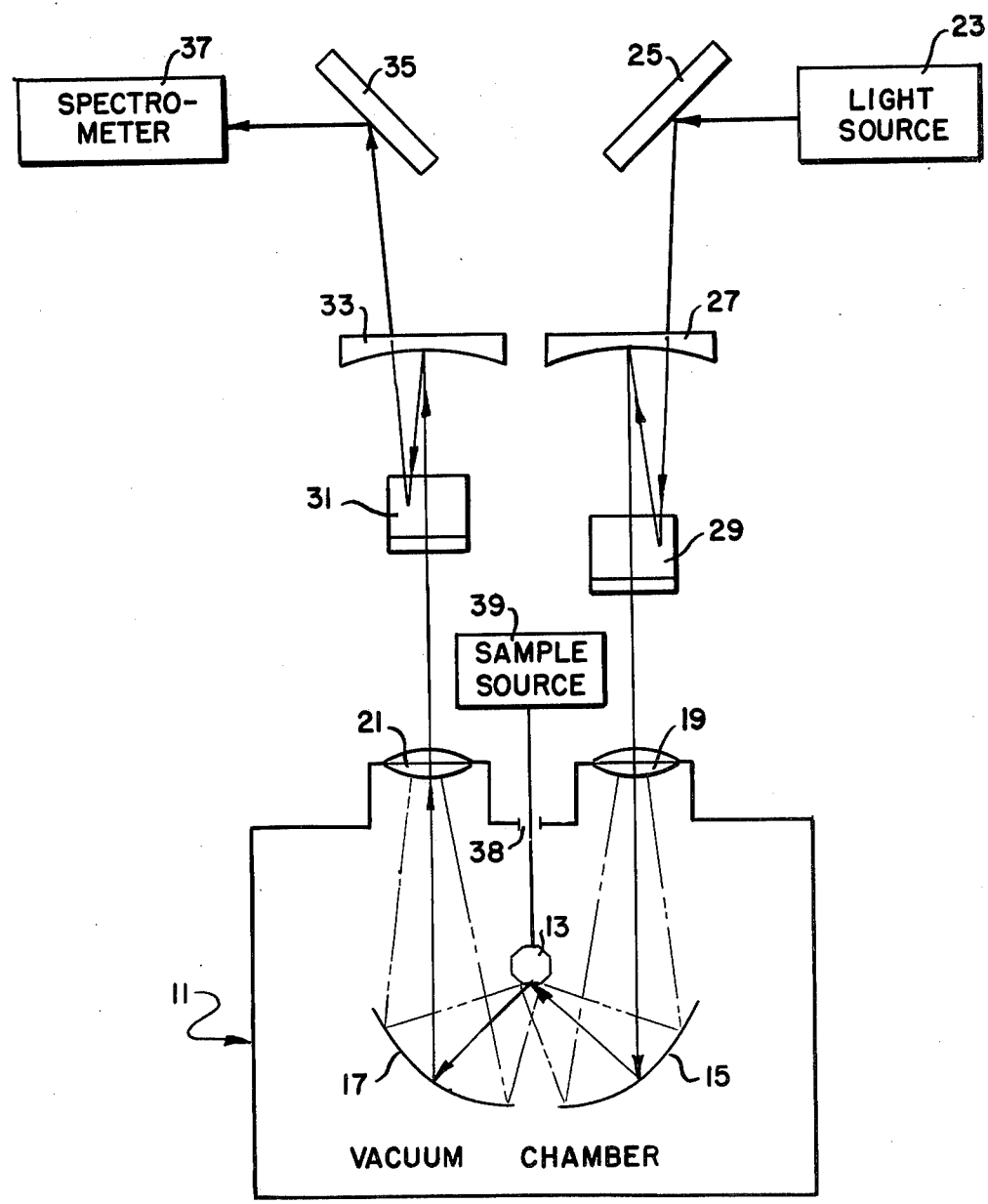
FIG. 1 is a schematic illustration of the optical path of one device for spectrometric examination of matrix-isolated samples.
Figure 2:
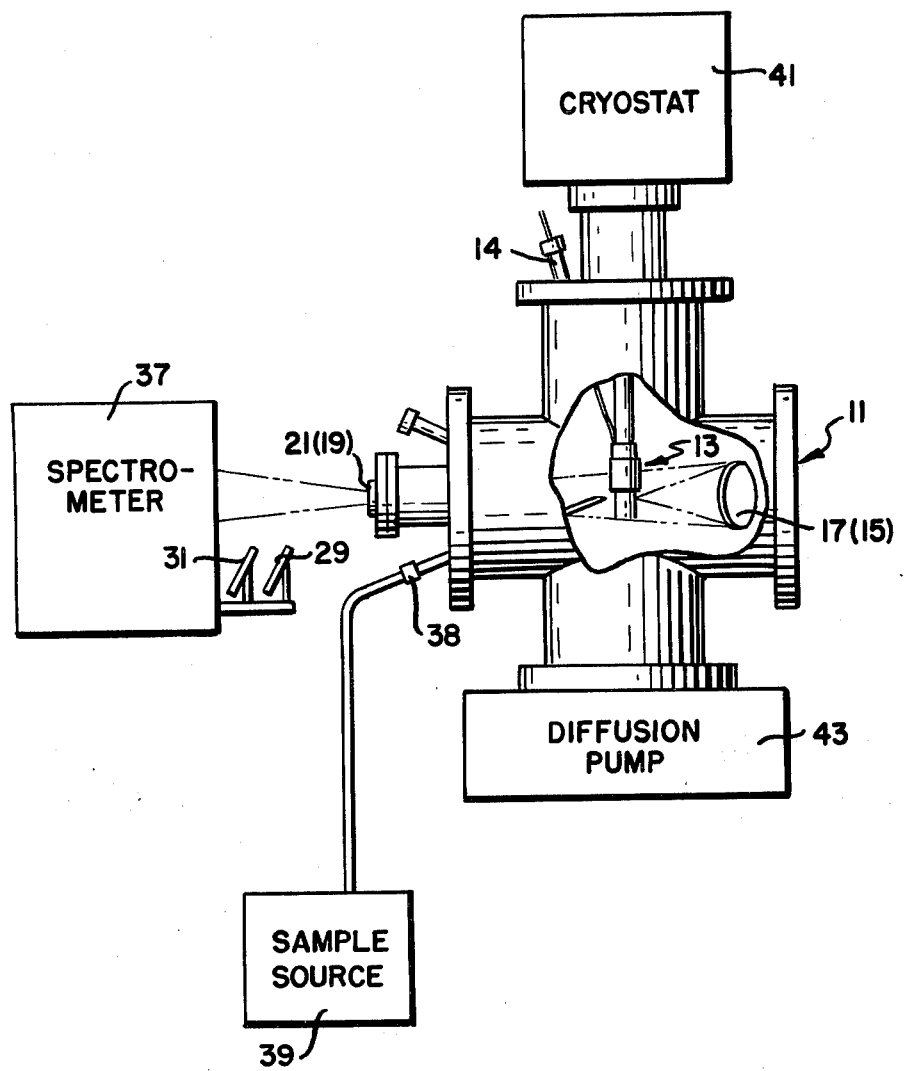
FIG. 2 is a side view illustration, partly broken away, of a sample collection device and spectrometer.

In FIGS. 1 and 2, the optical system of the present sample collection device is illustrated. A vacuum chamber 11 contains a specular carrousel 13 including a sample block having a plurality of sample surfaces as will be described below. Also shown enclosed within the vacuum chamber are two concave mirrors 15 and 17 aligned towards one of the sample surfaces of carrousel 13. Two lenses or optical windows 19 and 21 are installed within the vacuum chamber wall and aligned to admit and transmit light to and from the vacuum chamber 11. A beam of light is provided by light source 23 and transmitted into the vacuum chamber through, for instance, mirrors 25, 27 and 29. Similarly arranged mirrors, for instance 31, 33 and 35, can direct the return light beam into a spectrometer 37 for characterizing the spectra of the sample material. The particular system illustrated in FIG. 1 is suitable for characterizing infrared absorption spectra of samples.

Optical windows 19 and 21 can be convex lenses as illustrated for focusing the light beam. In some applications flat transparent plates may be suitable for use. The optical windows are of suitable transparent materials, e.g. polished potassium bromide for infrared light, glass or quartz for visible light and quartz for ultraviolet light.

Figure 4:
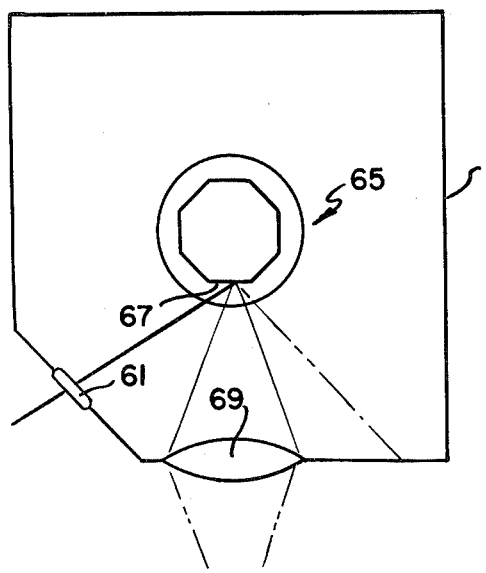
FIG. 4 is a schematic illustration of one modification to the optical path of FIG. 1.

Concave mirrors 15 and 17 are employed in the system illustrated in FIG. 1 to permit positioning the sample material on carrousel surfaces opposite to optical windows 19 and 21. In other modifications as illustrated in FIG. 4 the mirrors can be omitted. The mirrors 15 and 17 have spherical or ellipsoidal surfaces for directing and focusing the light beam between the optical windows 19, 21 and the sample on a reflecting surface of carrousel 13. Ellipsoidal surfaces, although difficult to fabricate, are of particular suitability as they can be arranged with one focal point at the sample on specular carrousel 13 and the second, at window 19 for mirror 15 and at window 21 for mirror 17. This can precisely focus the light beam through the sample to the optical elements leading to spectrometer 37.

In FIG. 2, the structural features of the sample collection device are more accurately illustrated. Gas samples for analysis are provided from a source 39 such as a gas chromatography unit through inlet 38 to the sample block surfaces. A cryostat 41 is shown for freezing the gaseous sample material onto an appropriate sample block surface and a diffusion pump 43 is connected into vacuum chamber 11 for maintaining a vacuum.

Many of the components illustrated in FIGS. 1 and 2 can be provided as conventional commercial devices. Gas sample source 39 will typically be a gas chromatography unit capable of separating gaseous components into distinct portions or bands that are sequentially discharged. As an example, a gas chromatography unit supplied by the Hewlett-Packard Company can be employed. Gas samples can be provided from other sources such as the decomposition or volatilization of sample material over a temperature range or as separate unrelated samples.

Spectrometer 37 also can be provided from well-known instruments such as a fourier-transform infrared spectrometer made available by Digilab Company or one of the numerous dispersion-type spectrometers.

Diffusion pump 43 can be any suitable commercially available pump that can provide vacuums of 1 to $10^{-4}$ microns Hg absolute within vacuum chamber 11. Cryostat 41 is also well known and can contain a refrigerant such as nitrogen or helium for obtaining temperatures of about 20 K to 4 K. For example, a helium closed cycle refrigerator as made available by Air Products Co. can be used.

Figure 3:
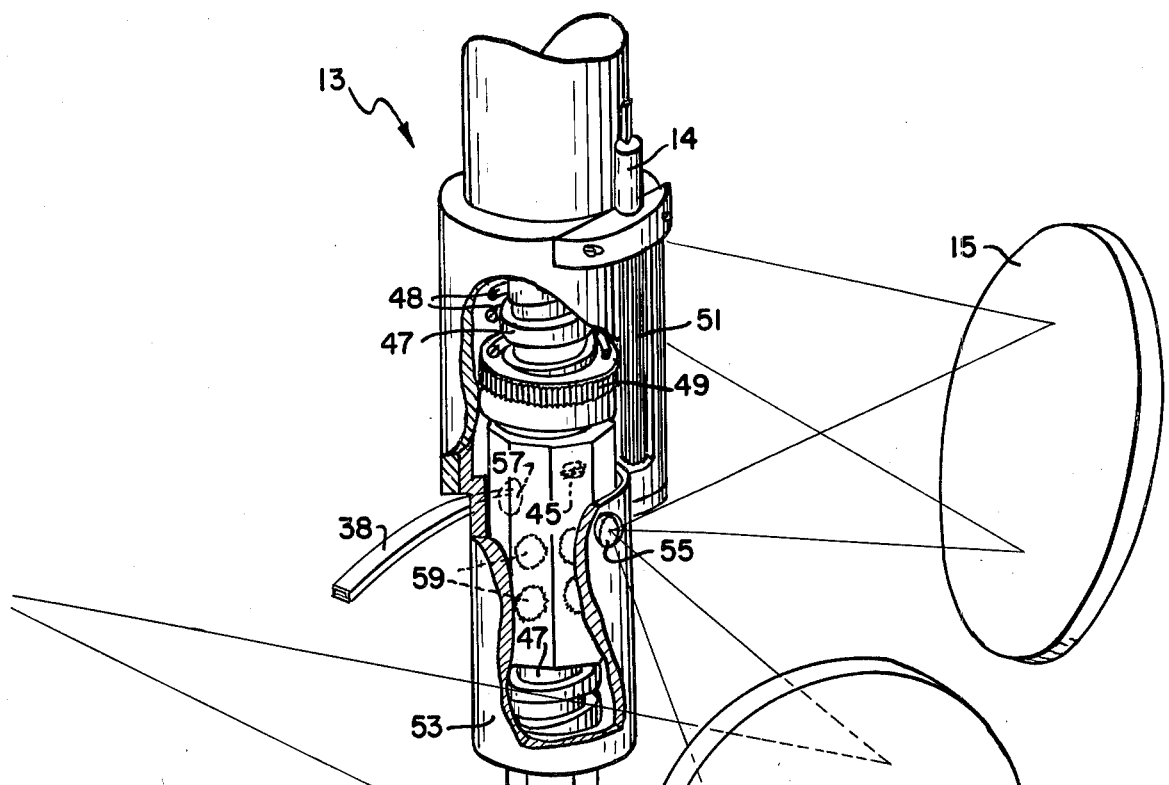
FIG. 3 is a fragmentary perspective illustration showing in more detail some of the components of FIG. 2.

In FIG. 3, the sample collection portion including the specular carrousel 13 is more clearly shown. Carrousel 13 has a longitudinally mounted sample block 45 shown threadedly engaging a stationary, spiral-screw shaft 47. Spur and pinion gears 49 and 51, respectively, are illustrated as one manner of transmitting rotation from drive shaft 14 to sample block 45. Spur gear 49 is shown fixedly mounted on sample block 45 so that it imparts rotation to the block. As block 45 rotates, it also translates longitudinally along spiral-screw shaft 47.

A coiled spring 48 is shown engaging and downwardly loading spur gear 49 to enhance conductive heat transfer communication between sample block 45 and spiral-screw shaft 47. Shaft 47 is stationarily mounted and is in conductive communication with the cold fluid within cryostat 41. Heat is thereby conducted from the reflecting surfaces of sample block 45 through shaft 47 to the refrigerant within cryostat 41.

Sample block 45 is illustrated as an octagonal prism with with eight longitudinal external surfaces. It will be clear that other prismatic shapes can also be employed with triangular, rectangular or various other polygonal end surfaces. The longitudinal external surfaces of sample block 45 include highly reflecting material such as gold plating.

The sample-block portion of carrousel 13 is enclosed within a shield 53 for excluding radiation and stray gas. Shield 53 is shown with an opening 55 directed towards concave mirrors 15 and 17 and a second opening 57 placed generally opposite to opening 55 for admitting the sample gas inlet 38. Other modifications also can be employed, for instance of depositing and examining the sample through the same opening with means provided for removing the sample gas inlet 38 when the examination is made.

Gas samples that have been separated into distinct components can be solidified on the cold surfaces of sample block 45. By rotating the sample block with drive shaft 14, new locations are exposed to sample inlet 38 by both rotational and translational motion of the block. Consequently a plurality of samples as illustrated at 59 can be captured and stored on sample block 45. When it is desired to present a particular sample for spectroscopic analysis, sample block 45 is rotated.

The samples illustrated at 59 include unknown sample material for analysis along with a frozen matrix material for isolating the sample. As an example, inert and neutral gases such as argon or krypton are quite suitable for use as matrix materials.

In the optical system of FIG. 1, a beam of electromagnetic radiation from source 23 is transmitted by means of mirrors 25, 27 and 29 into vacuum chamber 11 through optical window 19. The electromagnetic radiation is typically infrared light but in other than IR spectrometric analytical systems visible light or ultraviolet light may be employed. It is also contemplated that laser sources or light provided by the luminescence, fluorescence or phosphorescence of the sample might be used.

As illustrated, the light beam entering lens 19 is projected on concave mirror 15 within vacuum chamber 11. This mirror focuses the light onto and twice through sample material 59 deposited on one of the reflecting surfaces of sample block 45. The beam is reflected to the second concave mirror 17 from which it is focused through optical window 21 and transmitted by mirrors 31, 33 and 35 into a suitable spectrometer for characterization of absorption spectra.

In FIG. 4 a modification to the system described above is illustrated. A laser beam from a suitable source is transmitted through optical window 61 within the wall of vacuum chamber 63. The beam passes through a matrix-isolated sample on a reflecting surface 67 of specular carrousel 65. The specular carrousel 65 can be essentially as described above. The reflected portion of the beam is absorbed on suitable surfaces within the vacuum chamber walls or otherwise removed from the optical system. A second optical window 69 is positioned within the vacuum chamber walls to miss the reflected portion of the beam but to receive light scattered from the sample material, e.g. positioned generally parallel to and directly facing the sample surface as illustrated. This scattered radiation is transmitted to a spectrometer (not shown) for Raman spectroscopic examination of scattered light spectra.

Various other modifications in materials and structure will occur to those skilled in the art within the scope of the present invention. For instance, the stationary shaft 47 of specular carrousel 13 can rotatably support the sample block 45 on a suitable bearing structure if only one tier of sample surfaces is needed. Means other than coiled spring 48 can be employed to downwardly load sample block 45 and thereby enhance heat transfer to spiral-screw shaft 47. For example, additional weight, other spring-type configurations or pneumatic loading are contemplated. Various other arrangements of lenses and mirrors to direct and focus light beams to samples and spectroscopic devices also may be found appropriate for use.

As an example of the use of the present device for analyzing a gas mixture, a feed mixture of ortho, para, and o-p dichloro phenols in a tetrahydrofuran solution were separated into five bands within a gas chromatography unit. Peak 1 of the gas chromatogram included tetrahydrofuran, peak 2 gave orthochlorophenol, peak 3 2,4-dichlorophenol, and peak 5 parachlorophenol. Each of these component portions from the gas chromatogram was injected with approximately 300 proportional parts of argon gas and passed into vacuum chamber 11 where they were solidified on sample block 45 as discrete samples 59. Each of the bands were easily identified by infrared spectrometry. The differentiation of ortho and para chlorophenol isomers was readily accomplished by this highly sensitive matrix-isolation technique. This analysis would have been difficult, if not impossible, to accomplish by other techniques such as mass spectrometry.

It is therefore clear that the present invention provides a sample capturing and collection device that can be interposed between a gas chromatography and infrared spectrometry units. The samples are isolated with separate matrices and held for an extended period of time to permit high-resolution spectroscopic examination. Specific structural details of sample molecules can be obtained which in earlier systems may have gone unresolved.

The embodiments of the invention in which an exclusive property or privilege is claimed are defined as follows:

1. A sample collection device for isolating a plurality of distinct samples each in a separate matrix for spectrometric examination comprising:
   an enclosed vacuum chamber and means for evacuating gases from said chamber;
   a specular sample block rotatably supported on its longitudinal axis within said vacuum chamber, said sample block having a plurality of external, reflecting surfaces;
   inlet means for depositing and solidifying sample material intermixed within matrix material onto the reflecting surfaces of the sample block;
   a first optical window within the wall of said enclosed vacuum chamber for admitting a beam of electromagnetic radiation into said chamber and a second optical window disposed within the vacuum chamber wall for transmitting electromagnetic radiation that has interacted with a sample from the chamber;
   rotational means comprising a stationary shaft supporting said sample block along its longitudinal axis and a rotational drive engaging said block for rotating it in respect to the stationary shaft, said rotational means being capable of positioning individual reflecting surfaces for sample deposition and for spectroscopic examination; and
   spectrometric means for providing a beam of electromagnetic radiation to said first optical window and thereby through said sample material on a reflecting surface of the sample block and for examining electromagnetic radiation from said second optical window to determine spectral characteristics of said sample material.

2. The sample collection device of claim 1 wherein said inlet means is interconnected with the gas discharge of a gas chromatography unit to provide bands of distinct gas samples for deposition onto respective, external reflecting surfaces of said sample block.

3. The device of claim 1 wherein heat-transfer means are provided in conductive communication with said sample block to maintain said reflecting surfaces at a sufficiently low temperature to solidify sample material and matrix material on said reflecting surfaces.

4. The device of claim 3 wherein said rotational means comprises a stationary, spiral-screw threadedly engaging said sample block along its longitudinal axis, spring means for longitudinally urging said sample block into firm conductive engagement with the spiral-screw threads to enhance heat transfer from said reflecting surfaces to said heat-transfer means and to impart both longitudinal and rotational motion to said sample block for presenting a helical progression of reflecting surfaces for sample deposition and examination.

5. The device of claim 4 wherein said sample block is shaped as a polygonal prism with elongated reflecting surfaces extending between parallel end surfaces for providing a longitudinal array of sample locations along each reflecting surface, said sample locations accessible to said inlet means through the rotation of said block on said stationary, spiral-screw shaft.

6. The device of claim 5 wherein said sample block comprises an octagonal prismatic block having elongated rectangular reflecting surfaces extending between octagonal end surfaces.

7. The device of claim 1 wherein there is provided a first concave mirror located within said enclosed vacuum chamber aligned to receive a beam of electromagnetic radiation from said first lens and to focus that electromagnetic radiation onto one of said reflecting surfaces of the sample block, and a second concave mirror located within said enclosed vacuum chamber aligned to receive electromagnetic radiation reflected from said one sample-block surface and to focus that electromagnetic radiation towards said second optical window.

8. The device of claim 7 wherein said first and second concave mirrors are ellipsoidal surfaces of two individual ellipsoids, the first ellipsoid having focal points at the center of said first lens and at a point on the reflecting surface of said sample block positioned in view of said first mirror, said second ellipsoid having focal points at said one point on said sample-block surface and at the center of the second lens.

9. The device of claim 7 wherein said sample block is enclosed within a tubular shield for blocking radiation and stray gas, said shield having apertures alignable with generally opposing reflecting surfaces on said sample block, one of said apertures facing generally towards the first and second concave mirrors and a second of said apertures providing access for the sample inlet means.

10. The device of claim 1 wherein a laser beam is provided to said first optical window and said second optical window is aligned to miss the reflected portion of radiation from the sample block reflecting surface and to receive scattered radiation from said sample material to permit Raman spectroscopic examination of scattered spectra.

* * * * *